US00PP25774P3

(12) United States Plant Patent
Schoone

(10) Patent No.: US PP25,774 P3
(45) Date of Patent: Aug. 4, 2015

(54) ***PHALAENOPSIS* ORCHID PLANT NAMED 'SILENT SONG'**

(50) Latin Name: *Phalaenopsis hybrida*
Varietal Denomination: Silent Song

(71) Applicant: Floricultura, Heemskerk (NL)

(72) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 119 days.

(21) Appl. No.: 13/986,343

(22) Filed: Apr. 23, 2013

(65) Prior Publication Data

US 2013/0291261 P1 Oct. 31, 2013

Related U.S. Application Data

(60) Provisional application No. 61/638,143, filed on Apr. 25, 2012.

(30) Foreign Application Priority Data

Apr. 26, 2012 (NL) ..... PBR OPS0892

(51) Int. Cl.
*A01H 5/02* (2006.01)

(52) U.S. Cl.
USPC ..... Plt./311
CPC ..... *A01H 5/02* (2013.01)

(58) Field of Classification Search
USPC ..... Plt./311
CPC ..... A01H 5/02; A01H 5/00
See application file for complete search history.

(56) References Cited

U.S. PATENT DOCUMENTS

PP24,710 P3 * 7/2014 Schoone ..... Plt./311

* cited by examiner

*Primary Examiner* — June Hwu
(74) *Attorney, Agent, or Firm* — Foley & Lardner LLP; Sunit Talapatra

(57) ABSTRACT

A new and distinct *Phalaenopsis* plant named 'Silent Song' particularly characterized by flowers which are white with some yellow and red/purple in the labellum; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis hybrida.*

Variety denomination: 'Silent Song'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Silent Song'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Silent Song' is a product of a controlled breeding program conducted by the inventor, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Silent Song' originated from a cross made by the inventor in 1999 in Strengweg, Heemskerk, The Netherlands. The female or seed parent is the *Phalaenopsis* cultivar designated 'Zuma Camreal', unpatented. The male or pollen parent is the *Phalaenopsis* cultivar designated 'Musashino×Taisuco Windian', unpatented. The new *Phalaenopsis* 'Silent Song' was discovered and selected by the inventor as a single flowering plant within the progeny of the stated cross in a controlled environment in 2007 in Strengweg, Heemskerk, The Netherlands.

Asexual reproduction of the new *Phalaenopsis* cultivar by tissue culture (mericloning) was first performed in November, 2007 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true to type.

BRIEF DESCRIPTION OF THE INVENTION

The following traits have been repeatedly observed and are determined to be unique characteristics of 'Silent Song', which in combination distinguish this *Phalaenopsis* as a new and distinct cultivar:

1. flowers which are white with some yellow and red/purple in the labellum;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'Silent Song', the diameter of the flowers of the female parent 'Zuma Camreal' is about 7 cm and with the male parent 'Musashino× Taisuco Windian' it is about 11 cm, whereas the diameter of the flowers of 'Silent Song' is about 9 cm.

Presently, a commercial cultivar to which 'Silent Song' can be meaningfully compared is 'FLOR251744' (U.S. application Ser. No. 13/986,342). The plant size of 'FLOR251744' is larger than 'Silent Song'. Also the size of the flower of 'FLOR251744' is larger. The color yellow in the labellum of both plants also differs. 'FLOR251744' has green/yellow and 'Silent Song' has yellow/green.

BRIEF DESCRIPTION OF THE PHOTOGRAPHS

The accompanying photographs illustrate the overall appearance of the new *Phalaenopsis* 'Silent Song' showing the colors as true as is reasonably possible with colored reproductions of this type. Colors in the photographs may differ slightly from the color values cited in the detailed botanical description, which accurately describe the color of 'Silent Song'.

DETAILED BOTANICAL DESCRIPTION

Figure 1:
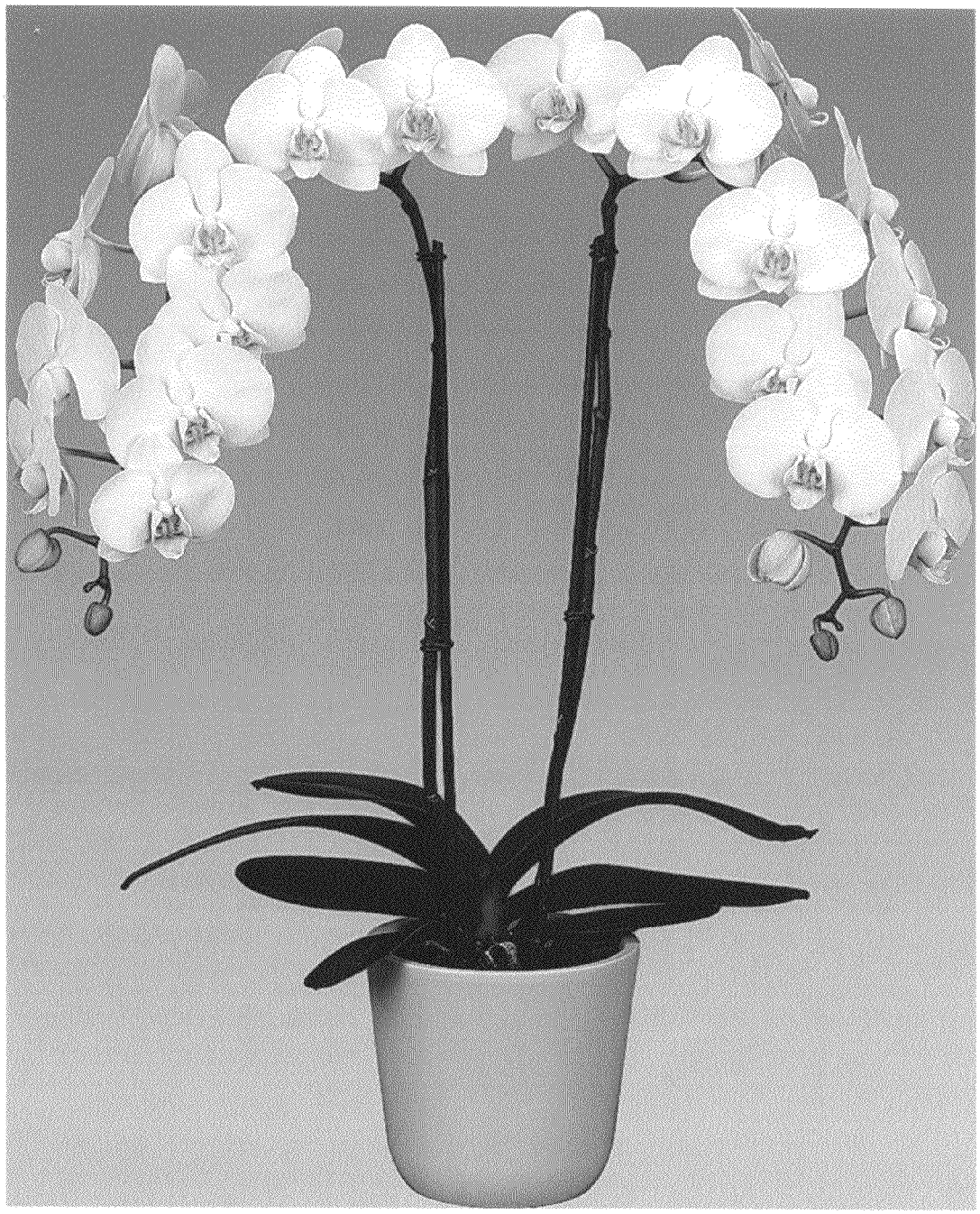
FIG. 1 shows a side view perspective of a typical flowering plant of 'Silent Song' in a 12 cm pot, at 16 months of age.

The new *Phalaenopsis* cultivar 'Silent Song' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Silent Song' as grown in a greenhouse in Strengweg, Heemskerk, The Netherlands, under conditions which closely approximate those generally used in commercial practice. Initially, the ideal temperature to grow plants of 'Silent Song' is 27° C. during the day and at night. Then, during the flowering phase of 'Silent Song', the ideal growing temperature is 20-22° C. during the day and 18° C. at night. Light levels for growing 'Silent Song' are a minimum of 5,000 lux and a maximum of 10,000 lux. A balanced fertilizer with level of 200 ppm N, 87 ppm P, 168 ppm K is applied. Duration of growth of 'Silent Song' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Silent Song' plants described is 12 months after potting.

Classification:

*Botanical.—Phalaenopsis hybrida.*

Parentage:

*Female or seed parent.—Phalaenopsis* cultivar designated 'Zuma Camreal', unpatented.

*Male or pollen parent.—Phalaenopsis* cultivar designated 'Musashino×Taisuco Windian', unpatented.

Propagation:

*Type.*—Tissue culture.

*Rooting habit and description.*—Fleshy; approximately 4 mm-8 mm wide and green in color (RHS 137C) outside the pot mainly a mixture of green and greyed/white (RHS 156D/RHS 128D); freely branching. It takes 12 weeks for plants growing in tissue culture to initiate roots.

Plant:

*Size at maturity.*—Height: about 60 to 70 cm. Spread: about 39 to 60 cm.

*Growth habit.*—Standard; dark green leaves (RHS N137A) and a relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 2 racemes with flowers appear.

Foliage:

*Quantity per plant.*—About 6 to 10 leaves are produced before flowering.

*Arrangement and attachment.*—Half up/horizontal and on two sides.

*Overall shape of leaf.*—Oval, the tip is blunt and asymmetric.

*Texture (upper & underside).*—Smooth and leathery.

*Pubescence.*—None.

*Mature leaf length.*—About 15 to 23 cm.

*Mature leaf width.*—About 7 to 10 mm.

*Mature leaf thickness.*—About 2 mm.

*Mature leaf color.*—Upper side: green (RHS N137A). Under side: green (RHS 138A) outer edge (RHS 137A).

*Leaf base.*—Acute.

*Margin.*—Entire.

*Venation.*—Pattern: parallel. Color of midvein: upper side: green (RHS N137A). Under side: green (RHS 144A).

Inflorescence description:

*Appearance.*—Upright to slightly pendant, racemose inflorescence with bilaterally symmetrical flowers that open in succession beginning with the lowermost flower.

*Buds.*—Height (from base to tip): about 29 cm. Diameter (at midpoint): about 24 cm. Shape: egg-shape/oval. Color: yellow/green (RHS 145C).

*Raceme*.—Quantity per plant: about 1 to 2. Number of flowers per raceme: about 9 to 14. Length: about 60 to 70 cm.

*Peduncle*.—Diameter: about 6 to 8 mm. Strength: strong. Aspect: upright. Texture: glabrous and smooth. Color: green (RHS 146A).

*Flowering time*.—For an untreated plant (flowering plant that has not undergone cold-treatment where the plant grows at a temperature of 18° C. to 19° C. for about 4 to 8 weeks after a period of about 30 weeks at a temperature of 25° C.), 2 racemes appear with flower buds and flowers. First flowers can be expected approximately 4 to 6 months after planting a plant with a leaf diameter of 3 to 5 cm. Flowers persistent.

*Flowering longevity*.—On the plant: about 4 to 6 months; lastingness of cut flowers: has not been observed.

*Fragrance*.—No fragrance.

Figure 2:
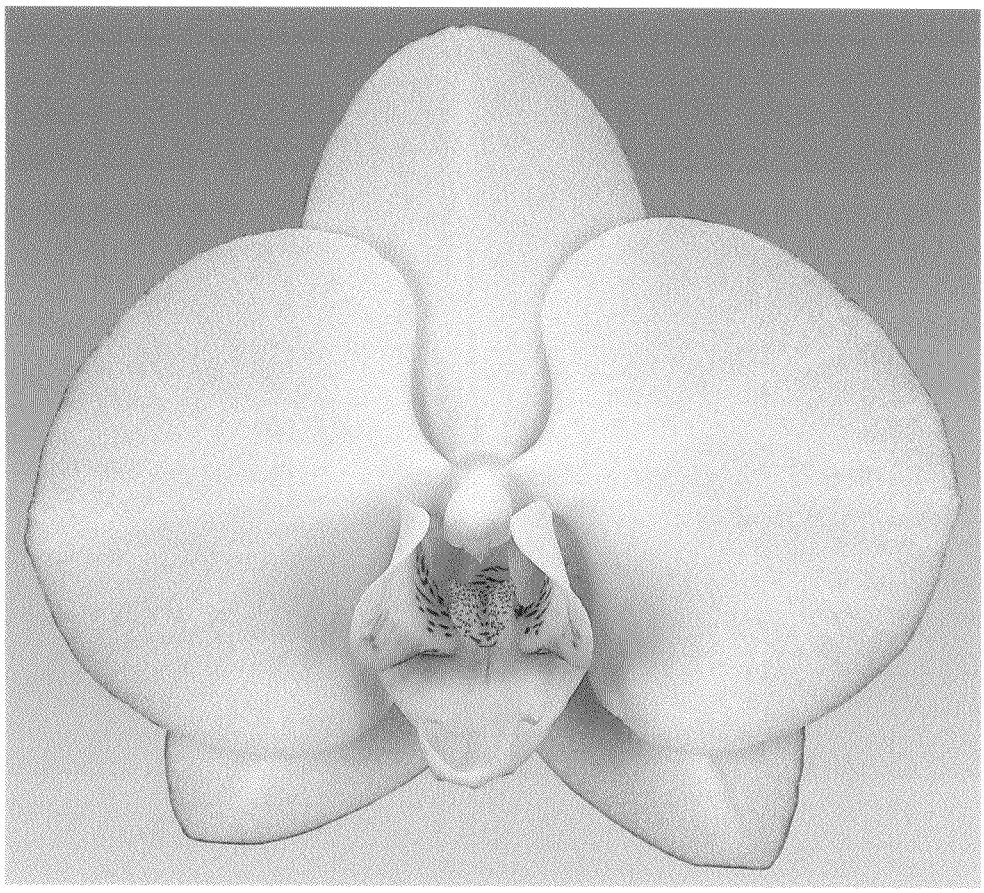
FIG. 2 shows a close-up view of a typical flower of 'Silent Song'.
Figure 3:
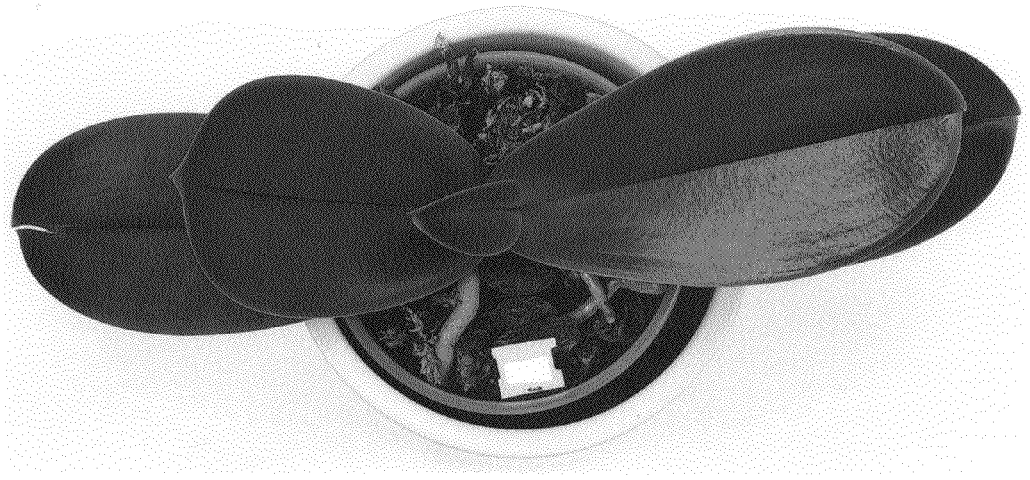
FIG. 3 shows a close-up view of the typical leaves of 'Silent Song'.

*Flower*.—Rate of opening: Flowers fully opened about 2 to 3 days after petal and sepal separation. Orientation at opening: slanted upward and outward. Shape: typical shape of *Phalaenopsis* orchid; see FIG. 2. Size: Height: about 65 mm to 75 mm. Diameter: about 80 mm to 90 mm. Quantity and arrangement: three petals and three sepals that are trimerous, overlapping and arranged in 2 whorls. Petals are more pronounced than sepals.

*Petals*.—Arrangement: Inner whorl comprises 3 petals: 2 lateral petals and a labellum. 2 lateral petals: Overall shape: broadly ovate. Apex: round with a small point. Margin: smooth and weakly undulate. Base: broadly ovate. Length: about 50 mm. Width: about 40 mm. Texture: Upper surface: smooth and satiny. Under surface: smooth and satiny. Color (when fully opened): upper side: White RHS NN155C. Under side: white RHS NN155C. Labellum: Overall shape: 3-lobed with 2 prominent callosities at central junction of the lateral lobes and base of the midlobe. Lateral lobes of labellum fold upward about the column; the midlobe extends forward and is terminated by 2 filiform appendages at the apex. Lateral lobes of the labellum are ovate in shape while the midlobe is triangular with a bump and a rib on it. Margin: entire. Apex: oval. Length midlobe: about 19 mm. Width midlobe (not flattened): about 22 mm. Length lateral lobe: about 17 mm. Width lateral lobe(not flattened): about 17 mm. Depth of tube created by lateral lobes of labellum: about 17 mm. Texture: Upper and under surface: smooth and satiny. Color (when fully opened): Midlobe: upper surface: main color is white (RHS NN155C). At the base and at the right and left corner yellow/green (RHS 2B) with small orange edges which runs out (RHS 26A). Some small vague purple/violet spots (RHS N80D). In the middle a small line (RHS 60C). Under surface: main color is white (RHS NN155C), left and right and slightly in the middle green/yellow (RHS 2B) with orange edges (RHS 26A) and purple veins (RHS N80D). Lateral lobes: upper surface: main color is white (RHS NN155C) below green/yellow (RHS 12A). At the base purple/grey spots (RHS 183D) and purple/violet stripes (RHS N80B). Lower small edge from base till almost the end is yellow (RHS 26A). Under surface: main color is white (RHS NN155C). Below green/yellow (RHS 12B) with light haze of purple/violet (RHS N80D). At the top a vague orange spot (RHS 26A and RHS N80A) At the base a clearer spot (RHS N80B). Cirrhi: about 15 mm (long and curly). Color: From white (RHS NN155C) to green/yellow (RHS 2B) with a little purple/violet (RHS N80D). Pestle (Callosities): Length: about 7 mm. Width (not flattened): about 5 mm. Color: main color is white (RHS NN155C). Edges and inside are yellow (RHS 13B) and spots and a stripe on the front are purple/grey (RHS 183D).

*Sepals*.—Arrangement: Outer whorl comprises 3 sepals: one dorsal and two lateral sepals. Overall shape: oval and weakly cupped, lateral more pointed than dorsal. Lateral is asymmetric. Margin: entire and weakly undulate. Length: about 41 mm. Width: about 30 mm. Apex: oval, lateral more pointed than dorsal. Texture: smooth. Upper and under surface: smooth and satiny. Color (when fully opened): upper side: main color is white (RHS NN155C) at the base of the lateral sepals (RHS 144C) which runs out into (RHS 1C). At the base of the dorsal sepal (RHS 144D). Under side: dorsal sepal: White (RHS NN155C) with a clear purple/violet haze (RHS N80B) and in the center a green/yellow haze (RHS 150B). Lateral: White (RHS NN155C) clear green haze (RHS 150B) at the base green (RHS N144C) and in the point some purple (RHS N80B).

*Pedicel*.—Length: about 40 to 60 mm. Diameter: about 2 to 6 mm. Texture: glabrous and smooth. Color: starts with green (RHS 138A) which runs into yellow/green (RHS 145B and RHS 145D) an then into purple/violet (RHS N80D).

Reproductive organs:

*Arrangement*.—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column*.—Length: about 10 mm. Diameter: about 6 mm. Color: white (RHS NN155C) and purple/violet spots (RHS N80B). Pollinia: Quantity: two. Diameter: about 1 mm. Color: orange (RHS 24A).

*Ovary*.—Length: about 3 mm. Diameter: about 5 mm. Color: white (RHS NN155C).

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Silent Song', as illustrated and described herein.

* * * * *